(12) United States Patent
Sitther et al.

(10) Patent No.: US 10,626,363 B2
(45) Date of Patent: Apr. 21, 2020

(54) ENGINEERED CYANOBACTERIA WITH ENHANCED SALT TOLERANCE

(71) Applicant: Morgan State University, Baltimore, MD (US)

(72) Inventors: Viji Sitther, Baltimore, MD (US); Behnam Tabatabai, Baltimore, MD (US)

(73) Assignee: Morgan State University, Baltimore, MD (US)

( * ) Notice: Subject to any disclaimer, the term of this patent is extended or adjusted under 35 U.S.C. 154(b) by 0 days.

(21) Appl. No.: 15/833,870

(22) Filed: Dec. 6, 2017

(65) Prior Publication Data
US 2018/0291332 A1 Oct. 11, 2018

Related U.S. Application Data (63) Continuation of application No. 14/873,879, filed on Oct. 2, 2015, now abandoned.

(60) Provisional application No. 62/060,229, filed on Oct. 6, 2014.

(51) Int. Cl.
C12N 1/13 (2006.01)
C12N 15/53 (2006.01)
C12N 15/63 (2006.01)
C12P 7/64 (2006.01)
C12N 1/20 (2006.01)
C07K 14/195 (2006.01)
C12R 1/01 (2006.01)

(52) U.S. Cl.
CPC .............. *C12N 1/20* (2013.01); *C07K 14/195* (2013.01); *C12P 7/6463* (2013.01); *C12R 1/01* (2013.01)

(58) Field of Classification Search
None
See application file for complete search history.

(56) References Cited

U.S. PATENT DOCUMENTS

| 2009/0203070 A1 | 8/2009 | Devroe et al. | |
| 2012/0142066 A1* | 6/2012 | Baier | C12N 9/0006 435/161 |
| 2013/0280793 A1* | 10/2013 | Brown | C12Y 102/01 435/257.2 |

OTHER PUBLICATIONS

Takeya et al., "Purification and Characterisation of Malate Dehydrogenase From *Synechocystis* sp. PCC 6803: Biochemical Barrier of the Oxidative", Front. Plant Sci. 9, Article 947, 2018 (Year: 2018).*

Singh et al., "The freshwater cyanobacterium Anabaena doliolum transformed with ApGSMT-DMT exhibited enhanced salt tolerance and protection to nitrogenase activity, but became halophilic", Microbiology 159:641-648, 2013 (Year: 2013).*

GenBank Accession No. AB059562.1, Oct. 2001, 2 pages (Year: 2001).*

Christine Nicole S. Santos, et al.; Combinatorial engineering of microbes for optimizing cellular phenotype; Current Opinion in Chemical Biology 2008, 12:168-176.

In Vitro Cell.Dev.Bio.-Animal; 2014 World Forum on Biology Abstract Issue; Plant Posters; Published online; May 14, 2014.

Tetsushi Sakiyama, et al; Functions of a hemolysin-like protein in the *Cyanobacterium synechocystis* sp. PCC 6803; Arch Microbiol (2011) 193: 565-571; Apr. 8, 2011.

Shailendra P. Singh, et al.; Salinity impacts photosynthetic pigmentation and cellular morphology changes by distinct mechanisms in Fremyella diplosiphon; Biochemical and Biophysical Research Communications 433 (2013) 84-89; Jan. 31, 2013.

Tadashi Matsunaga, et al; Genetic engineering in marine cyanobacteria; Journal of Applied Phycology 7: 77-84, 1995; Jun. 1, 1994.

* cited by examiner

*Primary Examiner* — David Steadman
(74) *Attorney, Agent, or Firm* — Sughrue Mion, PLLC (57) ABSTRACT

The present invention relates to a recombinant cyanobacterium with enhanced halotolerance and compositions thereof, methods of producing the recombinant cyanobacterium, and methods of using the same for biofuel production. The invention also relates to transformed *F. diplosiphon* strains with enhanced salt tolerance.

10 Claims, 5 Drawing Sheets

Specification includes a Sequence Listing.

SEQUENCE LISTING

<160> NUMBER OF SEQ ID NOS: 7

<210> SEQ ID NO 1
<211> LENGTH: 2431
<212> TYPE: DNA
<213> ORGANISM: Artificial Sequence
<220> FEATURE:
<223> OTHER INFORMATION: ApNhaP

<400> SEQUENCE: 1

```
gaattctgca ttcttccccc tgtttggtac aatcagtatg cccttgctac agtagtaaag      60
cggaatctct aagacaaacc agacatctgt ctcctgttgg aagataccaa agcggtattt     120
aactcactcc ccaaattaga agacaatata aaagaatcaa aaagcgttct gaggagaacc     180
attcatgttg cgaaaactta ttttaatcac agtggcgact gtgtttttg cctgtcaact      240 gcttgtcaac cctgtctctg ctttagaact cgatgaagaa agtcgcaccg ttcaatataa     300
tgaacaaggc gatgaagtcg tgattagtat taaagaagca gaaagaggga aacgtctctt     360
taacgacacc tgtgcacagt gtcatttagg tggtgtcact aaaaccaatc ccaacgttgg     420
cttgagttta gaagccttag agcgtgcaga acccctcgg gataatattg cagggttaat     480
tgattatatg aaaaacccca ccacttacga tggggaaatt gatattaaag agattcaccc     540
caataccgtg cgctctgata tcctacctga aaggagaaac ctaacggacg atgatctcga     600
agcgatcgcg gctcatattc tcagtcaacc gaaaagtccg aggaagcaat ggggtgacgg     660
taaagtctat aactaaggct taactgatga cctcaaagtc tgtctcgtgt ccctcctcat     720
gaatttgggg agggatttt agtacactat tacaaataaa cgtcacgatt aaagttacag     780
```

```
gaaagcctga tccctatgac tattgaagca gcaatgggag aagaagccat taaggaaaat      840
ttagaacagt tcctgattgt tctatcagtt tctttaggcg tagcaaccct ctcccaaatt      900
tccagtttct ttcgccaaat tccctatacg ttacttttgg ttattgttgg cttaggatta      960
gcatttgttg acatccgact cgttaatctt tctcccgaat taatcttaga aatcttttta     1020
cccccactct tatttgaagc agcgtggaat attcgctggc gtaatctcaa aaaaaattta     1080
tttcccgttg ttttacttgc cattattggg gttgttatat cagtggttgg gattggtttt     1140
agtctcaact attttagtgg cttatccctc cccattgctt tgttagtcgg tgctatttta     1200
gcagcaaccg atcctgtttc tgttattgct ttattccgag aactaggagt gggagaacgc     1260
ttaacggttc tcatggaagg agaaagttta tttaatgatg gtgttgcggt tgttgctttt     1320
agtctattag tgggaattcc cctcggaacg caagaatttt cggtcactaa taccctcatt     1380
caatttgtta ccttacaggg cattggcatc ggttgcgggg gcgttattgg ctttggaatt     1440
tcttatttaa cgcagcgttt tgatttgccc ttagtgaaac aatctctgac tttagtttct     1500
gcttacggaa cttatttaat cactgaagaa ttaggcggtt ctggtgtgat tggtgtggtg     1560
acagtcgggc taattttagg gaactttggc tctcgcattg gcatgaatcc gcggactcgt     1620
ttattagttt cagaattttg ggagttcatt gcttttttg tcaattcaat tgtctttctc     1680
ctgattggcg atcaaatcaa tattcgcggt ttagccgata tggacagtt aatttaatc     1740 acaattatcg ccctagtgat cattcgtgct atcagtattt atggcttagg aacaattagt     1800
aatttaatca cgaaacagga tattagttgg caagaagaaa cggttttatg gtggggcggt     1860
ttacgcggtt cggtttccat tgcgttggcg ttaagtgtcc ctgtcatgtt agatgggaga     1920
caagatatta ttgaagcggt gttggccgtt gtcctctta ccttgttagt ccaaggattg     1980
acgatgcaaa ccgttattga gaagctaggc ttaatcggcg atcgcgctca acgtcgtacc     2040
tatagcgaat taatcgcccg tcgcagtgcg ctcgaacggg ttttagccca cttaaatgcg     2100 gttccccct ccccagtat tagaatgaag agtttaaaga ctaccaagga ggcttcaaaa     2160
ggacaactcg aaagccgtca aaccaagaaa ctacgaagct acaacaattc ttatccccag     2220
ttacgatctt tagaacaaga acagctgcgg gaactaactt ttaaagtgga agcagacact     2280
tacgctgagt tgattcgggc gggtaaactc aataataatc tatctcccct attgcaagaa     2340
gtcctcgcca aaccagagtg agagggaaac aattatgttt cggtctcagg tgatcaagtg     2400
ctacgagtta ccctattgca ccctagaatt c                                   2431
```

<210> SEQ ID NO 2
<211> LENGTH: 1695
<212> TYPE: DNA
<213> ORGANISM: Artificial Sequence
<220> FEATURE:
<223> OTHER INFORMATION: BetT

<400> SEQUENCE: 2

```
atggttaaac aatcaaaacg tccagacttt gaagaggaac ttctggaaga acaaccagaa       60
cgttatcctg gtgataccaa cttccaaaaa tggggatttg atcttcatcc ccaagtcgca      120
cccatctctg ggggtttggt actcttattc attatcctca ctttaacttt taaagagcaa      180
gcctcctcgg tttttaacgc gactctcaac agcattgcca cctatggcgg ttggttttat      240
atcctcgctg caaacatctt ccttggcgtg gtcttaattt ttgcctttag taaatttggc      300
agaatccgtc tcggggggaca agatgcaaaa cctgaatttt ccacctttgc ttggtttgcg      360
```

```
atgctcctca gtgcaggaat ggggattggt ctaatgtttt ggagtgtggg agaacccatg    420
ttccacttta ttggccccccc tcccattttt ggctcggaag ctggaactcc tgatgctgcg    480
gaaaccgcaa tgacgattac gttttatcac tgggggcttc atccttgggg actctatgcc    540
ttagtgggac taggactcgc gttttttcgcc tttaatcgag gactccccct cacaatgcgc    600
tctgtatttt atcccctcct cggtgaaaga atttatgaat ggcctggtca cgtcattgac    660
attcttgccg ttgttgctga cttatttggt ttagccacct ccctcggttt agggtacag     720 caagttgcag ctggttaag ttttctcatt ccagcaatca atgaaggcgt aattacccaa     780
gtcaccttaa ttgcaattat tacaggcttt gctactttat ctgttgttgc tggtttagat    840
ggtggggtgc gtcgcctcag tgagtggaat ttgtatcttg ctgctacttt tatggtgttt    900
gtcctcgttt tagggccaac gctctttatt ttcgatacct ttgtccaaaa tattgggaat    960
tacgttgctc gtttcccat gctcagtttc tggactgaat cctttggatc aggagaagaa    1020
agcacctggc aaaatagttg gacggtcttt tattggggtt ggtggatttc ctggtctccg    1080
tttgtgggaa tgtttatcgc ccgtgttttcc agaggtcgta ccattcgtga atttgtgatg    1140
ggcgttctga ttgcacccac gcttctgtct tttctctggc tgtcaacaat gggcggagca    1200
gccttaaatc ttcagttaac caatgcagga gatattgctg ctgcggtgca agaaaacgtt    1260
gccacagcta tgtttgtgat gttggataac ttccccttaa cggcactaag ctccattgtg    1320
ggaattttac tggtgaccat cttctttgtc acttcctctg actcaggctc gctggttgtt    1380
gataatttga cttcaggggg aaaactggat tctcctgtac cacagcgagt gttttgggct    1440
gtgatggaag gtgtggttgc tgcggttttta ctccttggcg gtggcttaac ggctttacag    1500
acggctgcga ttacaacagg tttacctttt gcaattgtat tgctcatcat gttacagc     1560 ttgaatcaag ggctctcgca agaactacaa gaactagaaa tggcagaact gcgagatgct    1620
gaagccaaac gagaagaaaa aattgctgca attatggctt ctcgtcaaga agcgcgattt    1680
gcccaagatg aataa                                                      1695

<210> SEQ ID NO 3
<211> LENGTH: 350
<212> TYPE: DNA
<213> ORGANISM: Artificial Sequence
<220> FEATURE:
<223> OTHER INFORMATION: Mdh

<400> SEQUENCE: 3
atgttttatt catccgatcc gtctattgtt tgtagttttc ctcgcgtcag cattattggc     60
gcaggtagag ttggtagtac cctagcccaa cggattgctg agaaaaatct tgcagatgta    120
gttttattag atatcgtccc tggaatgcct caaggattgg cattggattt gatgagtct     180 agggggcattg aattacataa tcgtcggatt attggcacta acgattatat tgataccgca    240
ggttcagaaa ttgtggtgat tacagccgga cttccccgca aaccagggat gactagggat    300
gacttactga tcatcaatgc caagattgta gtagaagctg ccaagaatgc                350

<210> SEQ ID NO 4
<211> LENGTH: 1404
<212> TYPE: DNA
<213> ORGANISM: Artificial Sequence
<220> FEATURE:
<223> OTHER INFORMATION: ApNapA

<400> SEQUENCE: 4
atgacagctt tacaaacaat cttcaacac tctttatcgc ttaatcttga atcgggtctt     60
```

```
ccccttattag cgacagcttc tgaaacaact gcttccgaag cggatacaac cataattttg      120
gcaggggttt tactcagtct ggtctttatt tattttgcca gtaaattagg aggagaactc      180
tcaaaactgg ttgatttacc gcctgtttta ggagaattag tcgctggtgt tattgtcgga      240
atctccgctt tacatctggt cattttccca gaaacgggcg caatggcaag tgattcagtt      300
gttataacaa ttttgcagca agtggttggt ttacagccag aaaatgccag cgcagttttt      360
gccagtcaaa gtgaagttat ttcggtttta gctgaattag gggtgattat tctcctcttt      420
gaaattggct tagaatccga tttacgagag ttacaaaaag tgggcaccag agcagcgatc      480
gttgcggtga tcggcgttgt tgcaccccttt attgggggaa cggcgggatt aatgttactc      540
tttggaatgc caacgattcc cgccgttttt gcaggggcag cgttaaccgc caccagcatc      600
ggcattactt caaaagtgct ttcggaatta ggacaattaa agtccaaaga aggtcaaatt      660
attgttgggg ctgcggtgat tgatgatgtc ctagggatta ttgttttagc agttgtggca      720
agtttagcaa agacagggga agttgatgtt ctcaacttag tttatttaat tgttagtgct      780
tctgctttct tgttgggttc aatcttttta gggaagtttt ttaataaaag ttttgtcgcg      840
atcgcgcaaa agttacaaac ccgaggcaat cttgtcatcc cagctttaat cttttgcattt      900 ttaatggcat ttcttgccaa cgcaattcaa ttagaggcaa ttttgggagc atttgctgca      960
ggattagtgt tagatgaaac cgacaaacgg aaagaattag atcaacaaat tattcccatt     1020
gccgacattt tagttcccat cttttttgtc tccgttggcg caagagtgga tctcagtgtt     1080
ttgaatccta ccagcgcaga aaatcgtcaa ggtttgatta ttgctgctttt cttaattgtc     1140 gttgcgatta ttggcaaaat tatcagtggt tgggcaattt ttggcaaaga aaaggtcaac     1200
cgtttagcga ttggaattgg tatgattcct cgggggggaag tgggcttagt gtttgctgga     1260
attggtgctg ctagtggcat tttagataaa ccgttacaag ctgcggtgat tattatggtt     1320
attttgacca cgtttattgc accgcctctg ttgcgttttg cctttaagga agaagcagaa     1380
atcgtcgagg aaacaggaag ttaa                                            1404

<210> SEQ ID NO 5
<211> LENGTH: 798
<212> TYPE: DNA
<213> ORGANISM: Artificial Sequence
<220> FEATURE:
<223> OTHER INFORMATION: ApGMST

<400> SEQUENCE: 5
atggctatca aagaaaaaca agttcaagac tacggcgaga atcccattga agttcgcgat       60
agtgaccact accaaaatga gtacatcgaa ggctttgttg aaaagtggga tgaactgatt      120
aactggcacg cccgttctag cagcgaaggg gaattttta ttaaaacccct caaagaacac      180 ggtgcaaagc gtgtcctcga tgctgcaact ggaactggat tccactccat tcgtctcatt      240
gaagctggct ttgatgtcgc aagcgtcgat ggtagtgtgg aaatgctggt caaagcatttt     300 gaaaacgcca ctcgtaaaga ccaaatcctc agaaccgttc actctgactg gcgacaagtg      360
actcggcata ttcaggaacg gtttgatgca gtgatttgtc taggaaactc ctttactcac      420
ctcttctcag aagaagatcg tcgcaaaacc ctcgctgagt ctattccgt cttaaaacat      480 gacggaattt taattttaga ccaacggaat tatgacttga ttctggatga agggtttaag      540
agcaagcata cctactacta ctgtggcgat aatgtcaaag cagaacccga atatgttgat      600
gatgggttag cgcgtttccg ttacgaattc cctgatcaga gtgtttatca cctcaatatg      660
```

```
ttcccattgc ggaaagatta tgttcgtcgt ctgcttcatg aagtgggctt tcaagatatc    720
acgacttatg gtgatttcca agaaacctat catcaagatg atcccgactt ttatattcac    780
gttgcgaaaa aagattaa                                                  798
```

<210> SEQ ID NO 6
<211> LENGTH: 834
<212> TYPE: DNA
<213> ORGANISM: Artificial Sequence
<220> FEATURE:
<223> OTHER INFORMATION: ApDMT

<400> SEQUENCE: 6

```
atgactaaag cagacgcagt cgccaaacaa gcacaagatt actacgacag tggtagtgcc     60
gacggcttct actatcggat ttgggggga gaagatctcc acatcgggat ttataacacc    120
cctgatgaac caatttatga tgcaagtgtc cgcactgtca gtcgcatttg tgacaaaatt    180
aaaaattggc cagcaggaac caaggtgctt gaccttggcg caggttatgg tggctccgct    240
cgttatatgg caaagcatca cggctttgat gtggattgtt tgaatatcag tttggtacaa    300
aacgagcgca atcgccagat gaaccaagaa cagggactcg ctgataaaat tcgtgttttt    360
gacggcagtt ttgaagagtt acccttgaa aataagagtt acgatgttct ctggtcacaa    420
gattctatcc tccatagcgg gaatcgtcgg aaagtcatgg aagaagccga tcgcgtcctc    480
aagtctggag gcgattttgt ttttactgat cccatgcaaa ccgataattg tccagaaggg    540
gtcttagagc cagtcttagc tcggattcat ttagatagtt tgggttcagt tggtttctat    600
cgacaagtgg cggaagaact cggttgggaa tttgttgaat tgatgaaca aactcaccag    660 ttagttaacc actatagtcg agtgctgcaa gaactggaag cccattatga tcaattgcaa    720
cctgaatgct cgcaagaata tttagaccgc atgaaggttg gcttaaatca ctggattaat    780
gcaggtaaaa gtggttacat ggcttgggga attctcaagt tccacaaacc ctag          834
```

<210> SEQ ID NO 7
<211> LENGTH: 747
<212> TYPE: DNA
<213> ORGANISM: Artificial Sequence
<220> FEATURE:
<223> OTHER INFORMATION: HlyB

<400> SEQUENCE: 7

```
catatttgaa gcagtgctca caacattgcg gacttattta tttgtggata ctaccaaccg     60
cattgatatg agtttggggt cacaaattat tgaccaccta ctccgcctac cactacgcta    120
ttttgaaaag cgtccagttg gggaattatc aactcgaatt aacgaactag aaaatattcg    180
gcaattcctc acaggtacag ctttaactgt tggcttagat gcagtatttt cggtggttta    240
tatcatcgtt atgctgtttt acagttggca acttaccttg gtaggtttgg gtacaattcc    300
cgtatttgta attctgacat taattgcctc tccgactgta caaagacagt tacgcagtaa    360
agccgaacgg aactccgaaa cacagtccta tttagttgag gtaatgtccg ggattcaaac    420
agtgaaagcg caaaatatcg aattgcgatc gcgcttttct tggcaagaac gttatgctcg    480
atacgtagcg gctggattca aaactgttgt gacttctacc ttggctaact caactagtaa    540 cttttctcaat aaaattgagta gtttactagt gttgtgggtg ggagcttatt tagtacttaa    600
acaagaatta accttagggg aattaatcgc ctttagaatt atctctggtt acgttactag    660
tcctatcttg cgcttggctc aactttggca aagcttccaa gaaacagctt tatctttaga    720
gcggttaagc gatattgttg atacacc                                        747
```

ENGINEERED CYANOBACTERIA WITH ENHANCED SALT TOLERANCE

This application is a continuation of application Ser. No. 14/873,879, filed Oct. 2, 2015, which claims the benefit of provisional Application No. 62/060,229 filed Oct. 6, 2014, the disclosures of each of which are incorporated herein by reference in their entireties.

FIELD OF THE INVENTION

The present invention relates to a novel recombinant cyanobacterium with enhanced halotolerance, and compositions thereof. The present invention also relates to methods of producing the recombinant cyanobacterium, and using the recombinant cyanobacterium for producing biofuels.

BACKGROUND OF THE INVENTION

About 85% of mankind's current energy needs are met by fossil fuels. Green energy companies have gained momentum in recent years which has fueled interest in the use of alternative energies. While there is some resistance to biofuel development and production from some policy makers, the pursuit of alternative energy sources is only likely to intensify. This is primarily due to growing global concerns of pollution and greenhouse effects of petroleum-based energy. In addition, price instability caused by rising worldwide demand is likely to impact future world energy markets.

Further, there is growing recognition that petroleum is a finite resource. As the imbalance between supply and demand for petroleum-based energy continues to increase, prices will rise and consumers will demand alternatives. For these reasons, even large oil companies have invested in the biofuel market. Billions of dollars are already tied to the biofuel and alternative energy markets, and these will continue to grow at a faster pace than petroleum-based energy markets over the next decade.

Currently, the most common biofuel alternative to fossil fuels is produced by fermentation of edible crops, mainly sugarcane and corn. However, biofuel production from these sources has created widespread debate, as it displaces land needed for food production. The challenge remains to develop renewable energy industries which are operatively sustainable and cost-competitive with existing energy options.

Fresh water is required for various agricultural and human needs and its supply is limited. On the contrary, sea water is abundantly available and generating fuel from brackish water is a viable alternate to solve the energy crisis. Brackish water found in ocean bays and gulfs also provides an enormous opportunity. Furthermore, in winter, de-icing salts, mainly in the form of sodium chloride get washed downstream resulting in salting of streams and waterways. The salty runoff water could be used as a source for generating biofuel. With nearly three quarters of the earth's surface covered by oceans, finding ways to better utilize salt water is critical to sustaining humanity.

The use of photosynthetic algae and cyanobacteria (blue-green algae) has recently received widespread attention for significant biofuel production due to their rapid growth, lack of requirement for arable land, $CO_2$ fixation, and genetic tractability (journal.frontiersin.org/article/10.3389/fbioe.2013.00007/full). These organisms can inhabit a wide-range of environmental conditions and have evolved different mechanisms to sustain their photosynthesis.

In particular, *F. diplosiphon* has a light-dependent acclimation process known as complementary chromatic adaptation which gives it the flexibility to grow in varying light intensities. These organisms grow in aquatic ecosystems which allow the use of $CO_2$ at higher concentrations than that of ambient air and could potentially allow the use of concentrated $CO_2$ emissions from waste industrial sources. Standard oil yields from cyanobacteria/algae range from 1,000-6,500 gallons/acre/year. (Hannon, M. et al., "Biofuels from algae: challenges and potential," *Biofuels*, 1, 763-784 (2010); and *International Energy Outlook*. U.S. Energy Information Administration. 284 (2009)).

The Department of Energy estimates that oil yields from cyanobacteria/algae range from 1,000-6,500 gallons/acre/year (*National Algal Biofuels Technology Roadmap.* U.S. Department of Energy, Office of Energy Efficiency and Renewable Energy, Biomass Program, (2010)). Calculation and analysis of oil from lipids by Weyer and his team (Weyer, K. M. et al., "Theoretical maximum algal oil production," *Bio Energy Research*, 3, 204-213 (2009)) has estimated a theoretical yield of 38,000 gallons/acre/year and a current practical yield of 4,350-5,700 gallons/acre/year from cyanobacteria/algae.

Cyanobacteria convert light energy into chemical energy through photosynthesis. To inhabit a wide range of environmental conditions, these organisms have evolved different mechanisms to sustain their photosynthesis (Gutu, A. et al., "Emerging perspectives on the mechanisms, regulation, and distribution of light color acclimation in cyanobacteria," *Molecular Plant*, 5, 1-13 (2012); Montgomery, B. L., "Shedding new light on the regulation of complementary chromatic adaptation," *Central European Journal of Biology*, 3, 351-358(2008)).

Over $6 trillion is spent worldwide on energy, and even a small shift toward biofuel represents billions of dollars in this enormous market.

SUMMARY OF THE INVENTION

A first aspect of the invention relates to recombinant cyanobacteria with increased or enhanced halotolerance comprising at least one polynucleotide encoding a halotolerance gene, as well as and compositions thereof.

The halotolerance gene is selected from the group consisting of ApNhaP (SEQ ID NO: 1), BetT (SEQ ID NO: 2), Mdh (SEQ ID NO: 3), ApNapA (SEQ ID NO: 4), ApGMST (SEQ ID NO: 5), ApDMT (SEQ ID NO: 6), and HlyB (SEQ ID NO: 7), and the polynucleotide encoding the halotolerance gene may have a nucleotide sequence with at least 60%, 75%, 80%, 85%, 90%, 91%, 92%, 93%, 94%, 95%, 96%, 97%, 98%, 99%, or 99.9% identity to any one of the polynucleotide sequence encoding ApNhaP (SEQ ID NO: 1), BetT (SEQ ID NO: 2), Mdh (SEQ ID NO: 3), ApNapA (SEQ ID NO: 4), ApGMST (SEQ ID NO: 5), ApDMT (SEQ ID NO: 6), or HlyB (SEQ ID NO: 7).

In a particular embodiment, the polynucleotide encoding the halotolerance gene is at least 60%, 75%, 80%, 85%, 90%, 91%, 92%, 93%, 94%, 95%, 96%, 97%, 98%, 99%, or 99.9% identity to a polynucleotide encoding Mdh. In another embodiment, the polynucleotide encoding the halotolerance gene is at least 60%, 75%, 80%, 85%, 90%, 91%, 92%, 93%, 94%, 95%, 96%, 97%, 98%, 99%, or 99.9% identical to a polynucleotide encoding HlyB.

A second aspect of the invention relates to a method for producing a halotolerant recombinant cyanobacteria comprising at least one polynucleotide encoding a halotolerance gene into wild-type cyanobacterium.

A third aspect of the invention relates to a plasmid comprising at least one polynucleotide encoding a halotolerant gene, wherein the plasmid is transformed into cyanobacterium.

A fourth aspect of the invention relates to a method for producing biofuel by growing recombinant cyanobacteria in salt water and salt amended media, and isolating lipid produced from the recombinant cyanobacteria.

Furthermore, another aspect of the invention is the halotolerant strains of *F. diplosiphon*, HSF33-1 and HSF33-2, produced by methods of the present invention.

Cyanobacteria have a fast generation time and halotolerant strains, according to the present invention, can be grown in closed systems (e.g., ponds or photo bioreactors) or in sea water where the sodium chloride concentration is high. By engineering the halotolerance gene into *F. diplosiphon*, biofuel can be produced using naturally available sea water, which will be a cost-effective alternative to fossil fuels.

DETAILED DESCRIPTION OF THE INVENTION

Cyanobacteria provide very high levels of net energy; hence, converting biomass into fuel is much less energy-intensive than other methods of conversion. Yields from cyanobacteria even dwarf terrestrial biofuel crops such as high-yield plants like oil palm which yield 637 gallons/acre/year. While various researchers have aimed at increasing lipid content to enhance biodiesel production in other cyanobacterial species (Hellingwerf, K. J. et al., "Alternative routes to biofuels: light-driven biofuel formation from $CO_2$ and water based on the photanol approach," *Journal of Biotechnology*, 142, 87-90 (2009); Liu, X. et al., "Production and secretion of fatty acids in genetically engineered cyanobacteria," *Proceedings of the National Academy of Sciences*, 107, 1-6 (2010)), there have been no attempts to enhance halotolerance in *F. diplosiphon*.

The present inventors have discovered a solution for generating an alternative source of biofuel from cyanobacteria in saline water, which is otherwise unsuitable for irrigating crops or for any other purpose. Novel recombinant cyanobacteria, *F. diplosiphon*, with salt resistant properties for enhanced halotolerance is provided. Wildtype *F. diplosiphon* is intolerant to salt concentrations above 15 g/L NaCl in solid media and 10 g/L NaCl in liquid media (sea water salinity 35 g/L). Proteins involved in the stress response were identified by growing cyanobacterial colonies under various salt concentrations and then proteins were isolated and purified using 2-D gel electrophoresis. Different patterns of protein accumulation were identified and linked to abiotic stress tolerance in cyanobacteria. Gene candidates (ApNhaP (SEQ ID NO: 1), BetT (SEQ ID NO: 2), Mdh (SEQ ID NO: 3), ApNapA (SEQ ID NO: 4), ApGMST (SEQ ID NO: 5), ApDMT (SEQ ID NO: 6), and HlyB (SEQ ID NO: 7)) from halotolerant cyanobacterial species were isolated, sequence analyzed and at least one gene candidate was incorporated into plasmids, which were used to transform *F. diplosiphon* to facilitate growth in saline environments. Integration of the halotolerance gene was confirmed with RT-PCR and physiological evaluations were conducted. At least one candidate gene from *Aphanothece halophytica*, a highly halotolerant species which tolerates up to 70 g/L NaCl, was inserted into the wild type *F. diplosiphon* to develop a genetically transformed cyanobacteria strain with enhanced halotolerance.

To investigate tolerability, transformed lines of cyanobacteria were subjected to varying levels of salt media and changes in growth and physiological responses were evaluated. The biofuel efficacy of the halotolerant strains was tested. Subsequent production of biofuel included harvesting, biomass drying, chemical extraction, mechanical/enzymatic methods, with analysis using mass spectrometry/nuclear magnetic resonance spectroscopy. Therefore, construction of recombinant cyanobacteria comprising at least one halotolerance gene selected from the group consisting of ApNhaP (SEQ ID NO: 1), BetT (SEQ ID NO: 2), Mdh (SEQ ID NO: 3), ApNapA (SEQ ID NO: 4), ApGMST (SEQ ID NO: 5), ApDMT (SEQ ID NO: 6), and HlyB (SEQ ID NO: 7), represents a suitable method for lipid biofuel production.

A first aspect of the invention relates to a recombinant cyanobacterium comprising at least one halotolerance gene.

Cyanobacteria, also known as cyanophyta, is a phylum of bacteria that obtain their energy through photosynthesis. They are often called blue-green algae. Cyanobacteria require light, inorganic elements, water and a carbon source, generally $CO_2$, to metabolize and grow. One of the main products of this metabolic process is lipid that can be converted into biofuel.

Halotolerance is tolerance to ionic stress, or the ability of an organism to grow at salt concentrations higher than those required for growth. (DasSarma S. and Arora P. (2006) Halophiles. Encyclopedia of life sciences. Wiley, London; Oren A (2006) Life at high salt concentrations. In: Dworkin M (ed), The prokaryotes: a handbook on the biology of bacteria. Springer, N.Y., which are hereby expressly incorporated by reference in their entirety.) Halotolerant species tend to live in areas such as hyper saline lakes, coastal dunes, saline deserts, salt marshes, and inland salt seas and springs. Halophiles are organisms that live in highly saline environments, and require the salinity to survive, while halotolerant organisms (belonging to different domains of life) can grow under saline conditions, but do not require elevated concentrations of salt for growth.

"Recombinant" refers to polynucleotides synthesized or otherwise manipulated in vitro ("recombinant polynucleotides") and to methods of using recombinant polynucleotides to produce gene products encoded by those in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium." The gene is then expressed in the recombinant host cell to produce, e.g., a "recombinant protein." A recombinant polynucleotide may serve a non-coding function (e.g., promoter, origin of replication, ribosome-binding site, etc.) as well. "Polynucleotide" and "nucleic acid" refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T." The term "polynucleotide" may encompass a single nucleic acid or nucleic acid fragment as well as plural nucleic acids or nucleic acid fragments, and refers to an isolated molecule or construct, e.g., plasmid DNA (pDNA), or derivatives of pDNA (e.g., minicircles as described in (Darquet, A. M. et al., "A new DNA vehicle for nonviral gene delivery: supercoiled minicircle," *Gene Therapy*, 4, 1341-1349 (1997)) comprising a polynucleotide. "Sequence identity" refers to a relationship between two or more polynucleotide sequences or between two or more polypeptide sequences. When a position in one sequence is occupied by the same nucleic acid base or, amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window (e.g., sequence of Mdh or sequence of HlyB).

"Heterologous" refers to any additional biological components that are not identical with the subject biological component.

"Homolog" or "variant," as used herein, can be used interchangeably and refers to a polynucleotide or polypeptide that differs from the recited reference polynucleotide or polypeptide due to substitutions, deletions, insertions, and/or modifications of one or more nucleotide base(s) (with regard to a polynucleotide) or one or more amino acid(s) (with regard to a polypeptide). Variants or homologs may occur naturally or be produced with conventional molecular techniques known in the art.

Polynucleotide or polypeptide variants or homologs can exhibit at least about 60-70%, for example 75%, 80%, 85%, 90%, 91%, 92%, 93%, 94%, 95%, 96%, 97%, 98%, 99% or 99.9% sequence identity with identified polynucleotide or polypeptide.

"Purified" means that the polynucleotide or polypeptide or homolog or variant thereof, is substantially free of other biological material with which it is naturally associated, or free from other biological materials derived, e.g., a recombinant host cell that has been genetically engineered to have enhanced or increased halotolerance.

Cyanobacteria convert light energy into chemical energy through photosynthesis in their natural environment using phycobilisomes (PBS) (Staijier R. Y. et al., "Phototrophic Prokaryotes: The Cyanobacteria," *Annual Review of Microbiology*, 31, 225-274 (1997), which is hereby expressly incorporated by reference in its entirety). They inhabit a wide range of habitats including oceans, fresh water, and terrestrial ecosystems. Recently, there has been great interest in their practical applications, particularly as a renewable source of bioenergy (Abed et al., "Applications of cyanobacteria in biotechnology," *Journal of Applied Microbiology*, 106, 1-12 (2008), which is hereby expressly incorporated by reference in its entirety).

In order to inhabit a wide range of environmental conditions, cyanobacteria have evolved different mechanisms to sustain photosynthesis. Many cyanobacteria have a light-dependent acclimation process known as complementary chromatic adaptation (CCA), which provides the organism flexibility in the type of light it can absorb to optimize its growth in a range of environmental conditions to which it is exposed (Montgomery, B. L., "Shedding new light on the regulation of complementary chromatic adaptation," *Central European Journal of Biology*, 3, 351-358 (2008), which is expressly incorporated by reference in its entirety). CCA allows these organisms to live at various depths of the ocean, despite the varying intensities of light present (Postius et al., "$N_2$-fixation and complementary chromatic adaptation in non-heterocystous cyanobacteria from Lake Constance," *Microbial Ecology*, 37, 117-125 (2001), which is expressly incorporated by reference in its entirety).

Some genes and proteins involved in the CCA process including rcaE and FdtonB in *Fremyella diplosiphon* have been identified and studied (Bordowitz, J. R. and Montgomery, B. L., "Photoregulation of cellular morphology during complementary chromatic adaptation requires sensor-kinase-class protein RcaE in *Fremyella diplosiphon*," *Journal of Bacteriology*, 190, 4069-4074 (2008); Pattanaik, B. et al., "FdTonB is involved in the photoregulation of cellular morphology during complementary chromatic adaptation in *Fremyella diplosiphon*," *Microbiology*, 156, 731-741 (2010); Kehoe, D. M. et al., "Using molecular genetics to investigate complementary chromatic adaptation: Advances in transformation and complementation," *Methods in Enzymology*, 297, 279-290 (1998), which are hereby expressly incorporated by reference in their entireties). Bordowitz and Montgomery (2008) compared two different strains of *F. diplosiphon*, one with normal CCA responses and one that is lacking rcaE; they found that this protein had an essential role in light-dependent regulation of the cell's morphological characteristics in response to red or green light.

RcaE combines with rcaC and rcaF to form a complex that regulates transcription for altering pigmentation during CCA (Kehoe, D. M. and Gutu, A, "Responding to color: the regulation of complementary chromatic adaptation," *Annual Review of Plant Biology*, 57, 127-150 (2006), which is hereby expressly incorporated by reference in its entirety). FdtonB is a protein found to have an important role in green light dependent regulation of a cell's morphology in *F. diplosiphon* (Pattanaik, B. and Montgomery, B. L., "FdTonB is involved in the photoregulation of cellular morphology during complementary chromatic adaptation in *Fremyella diplosiphon*," *Microbiology*, 156, 731-741 (2010), which is hereby expressly incorporated by reference in its entirety). CCA is supported by the presence of essential pigments in cyanobacteria known as phycobiliproteins (PBP) that assist in photosynthesis (Bogorad, L., "Phycobiliproteins and Complementary Chromatic Adaptation," *Annual Review of Plant Physiology*, 26, 369-401 (1975), which is hereby expressly incorporated by reference in its entirety). These PBPs form PBS, which harvest light from the abiotic environment (Gutu, A. and Kehoe, D. M., "Emerging perspectives on the mechanisms, regulation, and distribution of light color acclimation in cyanobacteria," *Molecular Plant*, 5, 1-13 (2012), which is hereby expressly incorporated by reference in its entirety).

Recently, cyanobacteria have been used in environmental applications, including bioremediation of pollutants such as heavy metals (Prasanna, R. et al., "Cyanobacteria as potential options for environmental sustainability—promises and challenges," *Indian Journal of Microbiology*, 48, 89-94 (2008), which is hereby expressly incorporated by reference in its entirety) and in the production of highly efficient photosynthesis derived biofuels (Ducat, D. C., et al., "Engineering cyanobacteria to generate high value products," *Applied Microbiology*, 29, 95-103 (2010), which is hereby expressly incorporated by reference in its entirety).

*Fremyella diplosiphon* has phycoerythrin (PE) and phycocyanin (PC) pigments that allow adaptation of the cyanobacterium to a range of habitats. In addition, a highly halotolerant species (*Aphanothece halophytica*), which can help in identifying molecular mechanisms associated with survival in higher salt environments are also included in the present invention.

Salt-tolerant mechanisms can be introduced into *F. diplosiphon* to complement its ability to grow in a range of environments with different light parameters. Improving salt tolerance in cyanobacteria is highly beneficial for the cultivation of cyanobacteria for biofuel production in environments with higher salinity, such as a saltwater ponds or salty lands that cannot be used for agriculture.

In another embodiment, halotolerant strains of *F. diplosiphon* produced by the methods of the present invention are HSF33-1 and HSF33-2. HSF33-1 with overexpressed HlyB gene was deposited in NCBI GenBank (National Center for Biotechnology Information, National Library of Medicine, Building 38A, Bethesda, Md. 20894) with the registration number KR912179 on May 27, 2014. HSF33-2 with overexpressed Mdh gene was deposited in NCBI GenBank, National Center for Biotechnology Information, National Library of Medicine, Building 38A, Bethesda, Md. 20894 with the registration number KP036997.1 on Oct. 24, 2014.

In one embodiment the recombinant cyanobacterium is *Fremyella diplosiphon*. *F. diplosiphon* exhibits CCA which allows this species to live at various depths in a water body, despite varying intensities of light (Gutu, A. et al., "Emerging perspectives on the mechanisms, regulation, and distribution of light color acclimation in cyanobacteria," *Molecular Plant*, 5, 1-13(2012), which is hereby expressly incorporated by reference in its entirety). In addition, it has great potential as a production-scale biofuel agent since it can grow in light intensity as low as 15 µmol m$^{-2}$s$^{-1}$ and at an optimal temperature of 28° C. (Dubinsky, Z. et al., "Photoacclimation processes in phytoplankton: mechanisms, consequences, and applications," *Aquatic Microbial Ecology*, 56, 163-176 (2009); Singh, S. P. et al., "Salinity impacts photosynthetic pigmentation and cellular morphology changes by distinct mechanisms in *Fremyella diplosiphon*," *Biochemical and Biophysical Research Communications*, 433, 84-89 (2013), which are hereby expressly incorporated by reference in their entireties). However, studies have shown that salt has detrimental effects on *F. diplosiphon* (Tabatabai, B. et al., "Investigating salt tolerance in the cyanobacterium *Fremyella diplosiphon* as the basis for biotechnological development," *20th Annual Undergraduate and Graduate Research Symposium*, Baltimore, Md. (2013), which is hereby expressly incorporated by reference it its entirety).

By incorporating a salt tolerance gene, the cyanobacterium finds unique environmental applications in open or closed salt water pond systems that can be used for biofuel production. The technology can be further extended because sea water is made up of a solution of salts of nearly constant composition of seventy different elements (Matsunaga, T. et al., "Marine Microalgae," *Advances in Biochemical Engineering/Biotechnology*, 96, 165-188 (2005), which is hereby expressly incorporated by reference it its entirety), which will provide nutrients for growth of *F. diplosiphon*.

Exemplary halotolerance genes that may be used in the invention include ApNhaP (SEQ ID NO: 1), BetT (SEQ ID NO: 2), Mdh (SEQ ID NO: 3), ApNapA (SEQ ID NO: 4), ApGMST (SEQ ID NO: 5), ApDMT (SEQ ID NO: 6), and HlyB (SEQ ID NO: 7), and variants thereof.

In certain embodiments, the halotolerance gene may be isolated from *Aphanothece halophytica*. *A. halophytica* is a halotolerant cyanobacterium which can grow in a wide range of salinity from 0.25 to 3.0 M NaCl and in extreme alkaline conditions up to an external pH of 11.0. Na+/H+ antiporters of alkaliphilic *A. halophytica* may play a crucial role of Na+ efflux and of cytoplasmic pH homeostasis.

In another embodiment, the recombinant cyanobacterium of the present invention has a higher salt tolerance as compared to wild-type cyanobacterium.

The recombinant cyanobacterium can be made by using conventional molecular methods known in the art. For example, the recombinant cyanobacterium can be made by introducing a polynucleotide encoding a halotolerance gene into wild-type cyanobacterium. The polynucleotide encoding a halotolerance gene can also be integrated into the genome of the cyanobacterium in order to make a recombinant cyanobacterium.

The present invention also relates to compositions comprising a recombinant cyanobacterium produced by methods described herein. The compositions described herein may include a carrier or excipient suitable for the recombinant cyanobacterium. Non-limiting examples include, but are not limited to, buffered saline, seawater, and BG-11 media and combinations thereof.

A second aspect of the invention is related to a method for producing a halotolerant recombinant cyanobacterium. The method includes introducing a polynucleotide encoding a halotolerance gene into the cyanobacterium to produce a halotolerant recombinant cyanobacterium.

In one embodiment, the method for producing a halotolerant recombinant cyanobacterium according to the second aspect of the invention further includes a step of incorporating at least one polynucleotide encoding a halotolerance gene in one or more plasmids and a step of integrating the polynucleotide encoding a halotolerance gene into the genome of the cyanobacterium.

The present invention uses standard methods for transformation of prokaryotes are known in the art. (Berger, S. L. and Kimmel, A. R. (1987), Guide to Molecular Cloning Techniques, Methods in Enzymology Vol. 152, Academic Press, Inc., San Diego, Calif.; Sambrook et al. (1989), Molecular Cloning—A Laboratory Manual (2nd ed.) Vol. 1-3, Cold Spring Harbor Laboratory, Cold Spring Harbor Press, N.Y.; and Current Protocols in Molecular Biology, F. M. Ausubel et al., eds., Current Protocols, a joint venture between Greene Publishing Associates, Inc. and John Wiley & Sons, Inc., (through and including the 1997 Supplement), which are hereby expressly incorporated by reference in their entireties).

Non-limiting examples of transformation techniques that may be used in the present invention include, but are not limited to, direct incubation in the presence of exogenous DNA, transformation by heat-shock, transformation by electroporation, transformation by biolistic particle bombardment, transformation via addition of fusogenic agents (i.e., polyethylene glycol), conjugation with a heterologous microorganism, or transduction via viral particles.

The method according to the second aspect of the invention can further include a step of isolating or making a polynucleotide encoding a halotolerance gene and incorporating the nucleic acid in one or more plasmids. The method can further include a step of integrating the recombinant nucleic acid into the genome of the cyanobacterium.

A third aspect of the invention relates to a plasmid containing a polynucleotide encoding a halotolerance gene. The plasmid construct is such that it is capable of being transformed into a cyanobacterium.

Plasmids relevant to genetic engineering typically include at least two functional elements 1) an origin of replication enabling propagation of the DNA sequence in the host organism, and 2) a selective marker (for example an antibiotic resistance marker conferring resistance to ampicillin, kanamycin, zeocin, chloramphenicol, tetracycline, spectinomycin, and the like). Plasmids are often referred to as "cloning vectors" when their primary purpose is to enable propagation of a desired heterologous DNA insert. Plasmids can also include cis-acting regulatory sequences to direct transcription and translation of heterologous DNA inserts (for example, promoters, transcription terminators, ribosome binding sites); such plasmids are frequently referred to as "expression vectors." When plasmids contain functional elements that allow for propagation in more than one species, such plasmids are referred to as "shuttle vectors." Shuttle vectors are well known to those in the art.

The present invention also relates to compositions comprising one or more plasmid(s) or expression vector(s) described herein. The compositions described herein may include a carrier or excipient suitable for the plasmid(s) or expression vector(s). Non-limiting examples include, buffered saline, seawater, and BG-11 media, and combinations thereof.

In some embodiments, several genes of interest may be inserted into the cyanobacterium. Each gene of interest may be expressed on a unique plasmid or expressed as part of a single plasmid. In preferred embodiments, the desired biosynthetic pathways are encoded on multi-cistronic plasmid vectors. Useful expression vectors are designed internally and synthesized by external gene synthesis providers.

A fourth aspect of the invention relates to a method of producing biofuel using the recombinant cyanobacteria of the present invention. The method includes growing the recombinant cyanobacteria comprising at least one nucleotide encoding a halotolerance gene under conditions suitable for production of a lipid for said biofuel production, and isolating the lipid.

Unless defined otherwise, all technical and scientific terms used herein have the meaning commonly understood by a person skilled in the art to which this invention belongs.

EXAMPLES

Example 1: Effect of Different Salt Concentrations on Cyanobacterial Growth

High levels of salinity cause a stress response in cyanobacteria, leading to an overexpression of certain proteins, particularly in more salt tolerant strains. High amounts of salt present in the environment can lead to diminished growth and viability in *F. diplosiphon*.

Preliminary results have demonstrated that *F. diplosiphon* does not tolerate salt concentrations above 15 g/L NaCl in solid media and 10 g/L NaCl in liquid media. The salinity of sea water is around 35 g/L which is more than twice the concentration that *F. diplosiphon* can tolerate. Thus, the key to unlocking this promising new source of energy is to enhance salt tolerance in this species.

Figure 1:
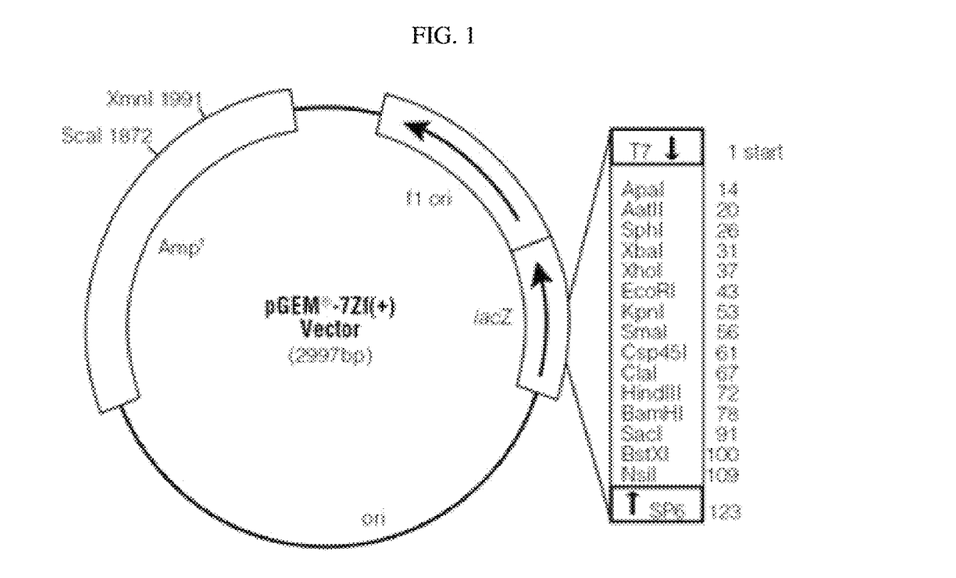
FIG. 1 shows the pGEM-7Zf (+) expression vector which was used to construct the recombinant plasmid.
Figure 2:
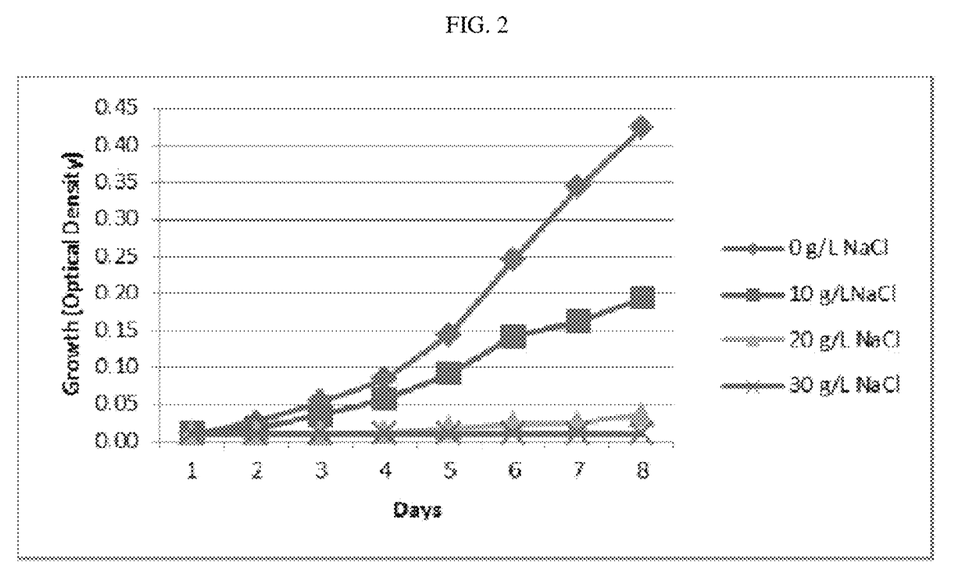
FIG. 2 shows the impact of salt on growth of *Fremyella diplosiphon* in 0 to 30 g/L NaCl in BG-11 liquid medium.

Cyanobacterial species *F. diplosiphon* were cultivated on liquid and solid growth medium with varying concentrations of sodium chloride. See FIGS. 2A and 2B. Determination of growth rates in various salt concentrations were compared to the control (absence of salt). In liquid cultures, the optical density of the cyanobacterial cultures (growth rate and doubling time) was measured.

Cyanobacteria were also subjected to varying light intensities and colors both in the absence and presence of salt to study to test differential responses of the cyanobacteria to the abiotic environment and to see if there is a link between light and salt stress responses.

Example 2: Genetic Transformation of Wild Type *F. diplosiphon*

Candidate genes, such as, ApNhaP (SEQ ID NO: 1), BetT (SEQ ID NO: 2), Mdh (SEQ ID NO: 3), ApNapA (SEQ ID NO: 4), ApGMST (SEQ ID NO: 5), ApDMT (SEQ ID NO: 6), and HlyB (SEQ ID NO: 7) from halotolerant cyanobacterial species were used to transform *F. diplosiphon* to complement its ability to grow in saline environments (Kehoe, D. M. et al., "Using molecular genetics to investigate complementary chromatic adaptation: Advances in transformation and complementation," *Methods in Enzymology*, 297, 279-290 (1998) which are hereby expressly incorporated by reference in their entireties).

Other candidate genes were also identified using the methods disclosed, for example, in Example 3, and transformed into *F. diplosiphon*.

Figure 3:
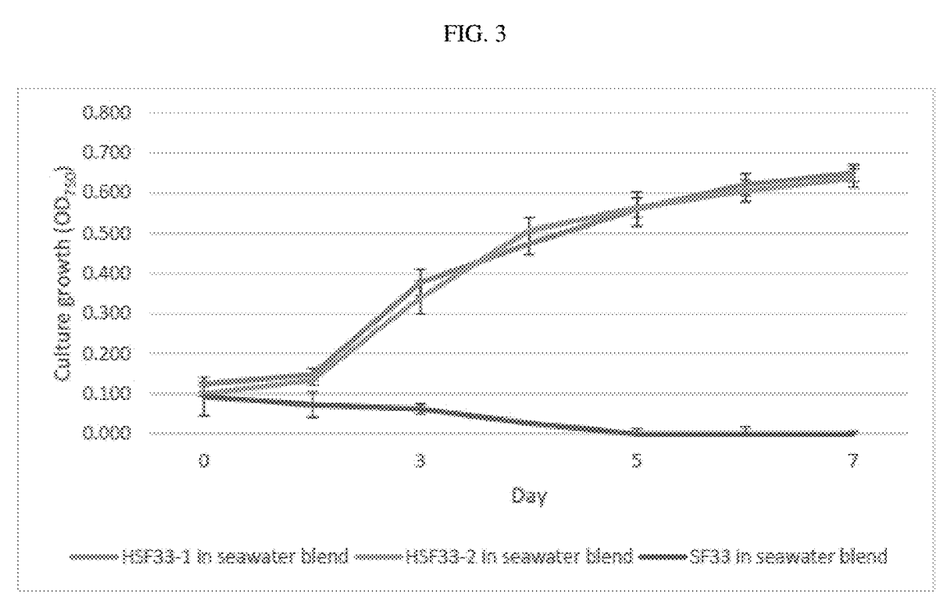
FIG. 3 shows growth of SF33, HSF33-1 and HSF33-2 in seawater blends after 7 days.

*F. diplosiphon* with the integrated halotolerance gene were screened and the presence of the gene was confirmed using RT-PCR. Physiological evaluations of transformed lines were then conducted (FIG. 3). Molecular screening is a quick and direct process and the tests could be conducted multiple times with each gene.

Additionally, candidate genes from *Aphanothece halophytica*, a highly halotolerant species that tolerates up to 175 g/L NaCl were inserted into the wild type *F. diplosiphon* in order to develop a genetically transformed strain with enhanced halotolerance (He, Y. et al. "Heterologous expression of ApGSMT2 and ApDMT2 genes from *Aphanothece halophytica* enhanced drought tolerance in transgenic tobacco." *Molecular Biology Reports*, 38, 657-666 (2010); Laloknam, S. et al., "Halotolerant cyanobacterium *Aphanothece halophytica* contains a betaine transporter active at alkaline pH and high salinity," *Applied Environmental Microbiology*, 72, 6018-6026 (2006), which are hereby expressly incorporated by reference in their entireties).

Example 3: Identifying Proteins Involved in Stress Response

Cyanobacterial colonies grown under various light and salt parameters were subjected to proteomic analysis. Proteins were isolated using a protein isolation and purification kit. The purified protein extracts were then run in one and two dimensional gels and then analyzed for bands and spots exhibiting differential patterns of protein accumulation. The spots representing these proteins were then identified, and linked to abiotic stress tolerance in cyanobacteria.

Once the candidate proteins were identified, the corresponding genes were isolated and sequence analyzed. These gene sequences were used to transform *F. diplosiphon* (Kehoe, D. M. et al., "Using molecular genetics to investigate complementary chromatic adaptation: Advances in transformation and complementation," *Methods in Enzymol-* ogy, 297, 279-290 (1998), which is hereby expressly incorporated by reference in its entireties for increased salt tolerance).

Genetically transformed cyanobacterial strains obtained by transformation have various applications in efficient biofuel production as they maximize growth rate and photosynthetic efficiency. The strategies described above can be extended to other cyanobacteria and used for efficient biofuel production.

Example 4: Extraction of Lipids from Wild Type and Halotolerant Strains

Figure 4A:
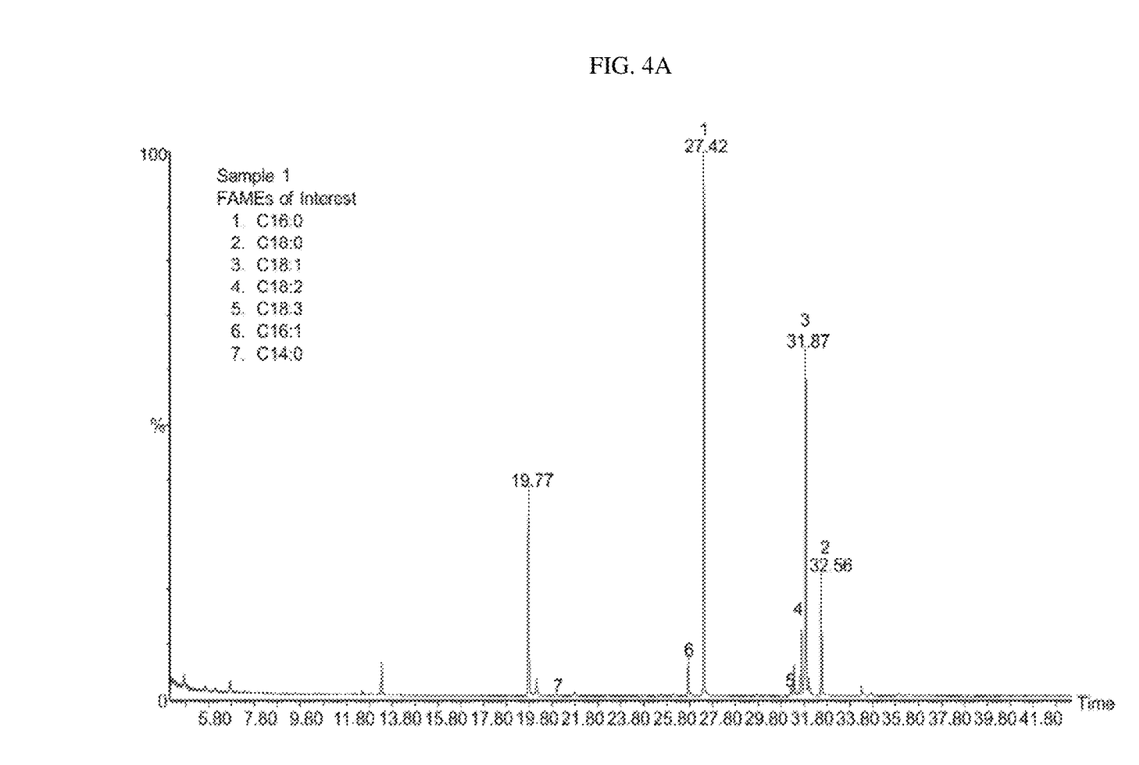
FIG. 4A shows the lipid profile of HSF33-1 and FIG. 4B shows the lipid profile of HSF33-2 via gas chromatograph mass spectra of peaks associated with methyl palmitate (C16:0) and other fatty acid methyl esters (FAMEs) (FIG. 4B).
Figure 4B:
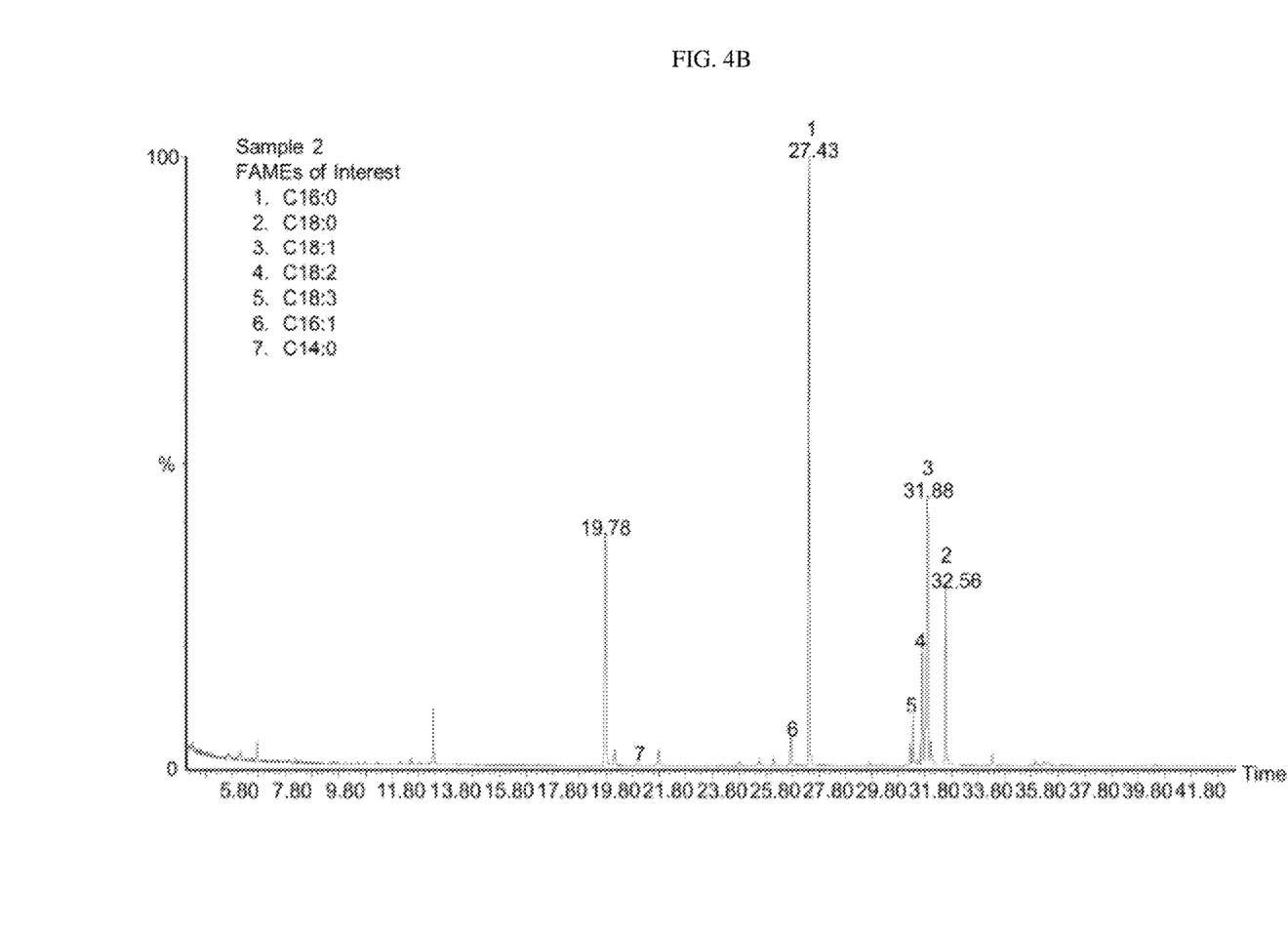

Lipids were extracted from the wild type (SF33) and halotolerant strains at the laboratory-scale level and lipid profiles are characterized using gas chromatography-mass spectrometry. See FIGS. 4A and B.

Transformed lines were subjected to varying levels of salt media following which growth and physiological response were investigated. The biofuel efficacy of the halotolerant strain was tested in controlled laboratory tanks where environmental conditions were monitored. Steps in biofuel production involve harvesting biomass, drying, extraction using chemical, mechanical or enzymatic methods, and analysis of lipids using mass spectrometry and Nuclear Magnetic Resonance (NMR) spectroscopy.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

Example 5: Aeration for Speedy Growth

Wild type (SF33) and halotolerant strains were cultured under two different growth conditions in liquid media, shaking at 170 rpm in a temperature-controlled shaker, and aeration using air pumps. Growth rates were compared and minimal time taken was estimated.

Example 6: Nitrate Level Alterations and Pigment Quantifications in the Salt Tolerant Strains Wild type (SF33) and halotolerant strains were grown in varying amounts of sodium nitrate at 0.25 g/L, 0.5 g/L, 1.0 g/L and 1.5 (control) g/L. Lipids, phycobiliproteins, and photosynthetic pigments (chlorophyll a, carotenoids) were extracted and quantified at the laboratory-scale level.

The amount and presence of fatty acid and methyl esters produced in varying amounts of sodium nitrate were estimated by gravimetric analysis and gas chromatography-mass spectrometry.

Example 7: Alum Precipitation

The wild type (SF33) and transformant cyanobacteria were harvested by adding varying concentrations of Aluminum sulphate (alum). Efficacy of alum concentration (1-5% (w/v)) in flocculating cells was estimated.

The amount and presence of fatty acid and methyl esters produced in flocculants precipitated in varying concentrations of Alum were estimated by gravimetric analysis and gas chromatography-mass spectrometry.

What is claimed:

1. A recombinant strain of *Fremyella diplosiphon*, wherein the recombinant strain of *Fremyella diplosiphon* is transformed with an exogenous polynucleotide encoding a halotolerance protein,
wherein said polynucleotide comprises the nucleotide sequence of SEQ ID NO: 3, and
wherein transformation with the exogenous polynucleotide encoding the halotolerance protein increases the salt tolerance of the recombinant strain of *F. diplosiphon* as compared to wild-type *F. diplosiphon*.

2. The recombinant strain of *F. diplosiphon* according to claim 1, wherein said polynucleotide is present in a plasmid or is integrated into the genome of said strain.

3. A method for producing a lipid, comprising:
growing the recombinant strain of *F. diplosiphon* of claim 1 under conditions suitable for production of a lipid; and
isolating the lipid.

4. The method according to claim 3, wherein said polynucleotide is present in a plasmid or is integrated into the genome of said strain.

5. A method for producing a halotolerant recombinant *Fremyella diplosiphon* comprising:
transforming an *F. diplosiphon* with a polynucleotide encoding a halotolerance protein to thereby produce a halotolerant recombinant *F. diplosiphon*,
wherein said polynucleotide comprises the nucleotide sequence of SEQ ID NO: 3.

6. The method for producing a halotolerant recombinant *F. diplosiphon* according to claim 5, wherein the recombinant *F. diplosiphon* has a higher salt tolerance as compared to wild-type *F. diplosiphon*.

7. The method for producing a halotolerant recombinant *F. diplosiphon* according to claim 5, wherein said polynucleotide is present in a plasmid or is integrated into the genome of said strain.

8. A recombinant strain of *F. diplosiphon* deposited with the National Center for Biotechnology Information under Accession number KP036997.1.

9. A composition comprising the recombinant strain of *F. diplosiphon* of claim 1.

10. A composition comprising the recombinant strain of *F. diplosiphon* of claim 8.

* * * * *